United States Patent [19]

Byrne

[11] Patent Number: 5,294,973
[45] Date of Patent: Mar. 15, 1994

[54] METHOD AND APPARATUS FOR DETERMINING BODY PLY CORD DISTRIBUTION

[75] Inventor: Francis J. Byrne, Olmsted Twp., Ohio

[73] Assignee: Bridgestone/Firestone, Inc., Akron, Ohio

[21] Appl. No.: 982,353

[22] Filed: Nov. 27, 1992

[51] Int. Cl.$^5$ .................... G01B 11/00; G01N 21/88
[52] U.S. Cl. .................... 356/372; 356/375; 348/88; 348/92
[58] Field of Search .............. 356/372, 375, 237; 358/101, 106, 107; 382/8

[56] References Cited

U.S. PATENT DOCUMENTS

| | | | |
|---|---|---|---|
| 3,734,624 | 5/1973 | Cornelius | |
| 3,918,816 | 11/1975 | Foster et al. | 356/4 |
| 4,277,178 | 7/1981 | Cushing et al. | 356/431 |
| 4,475,815 | 10/1984 | Takasu et al. | 356/385 |
| 4,857,749 | 8/1989 | McCarty | 250/571 |
| 4,980,902 | 12/1990 | Hegland et al. | 378/61 |
| 5,206,720 | 4/1993 | Clothiaux et al. | 358/101 |

Primary Examiner—F. L. Evans
Attorney, Agent, or Firm—David A. Thomas

[57] ABSTRACT

An apparatus and a technique for determining body ply cord distribution in a calendered fabric sheet. Test strips are cut from the sheet and formed in a roll with the cords extending parallel to the axis of the roll and normal to the end thereof. The end of the roll is then exposed to polarized light, accentuating light intensity differences between the cross sectional area of the cut cords and the elastomeric material in which they are embedded. A digitized image of the spiral end of the roll is generated and the resulting pixels are analyzed to determine the locations of the center points of each of the cords. Finally, the distances separating the center points of adjacent cords are determined and, if they fall above or below predetermined thresholds, a determination is made that the calendered fabric sheet is not acceptable for forming body plies.

20 Claims, 2 Drawing Sheets

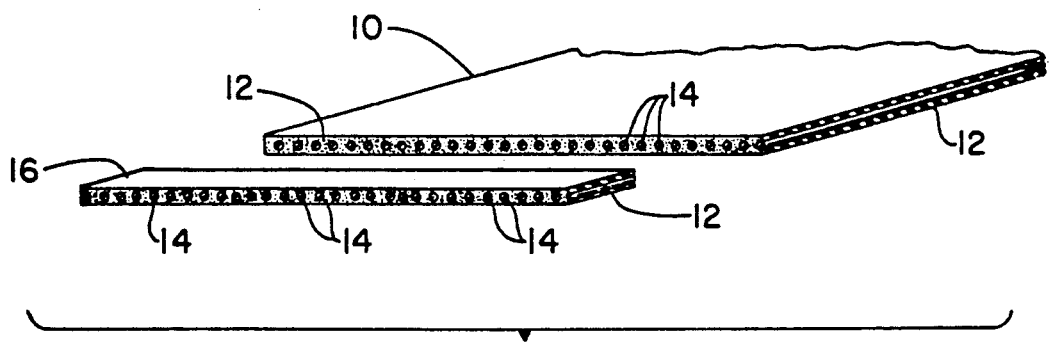
FIG.-1
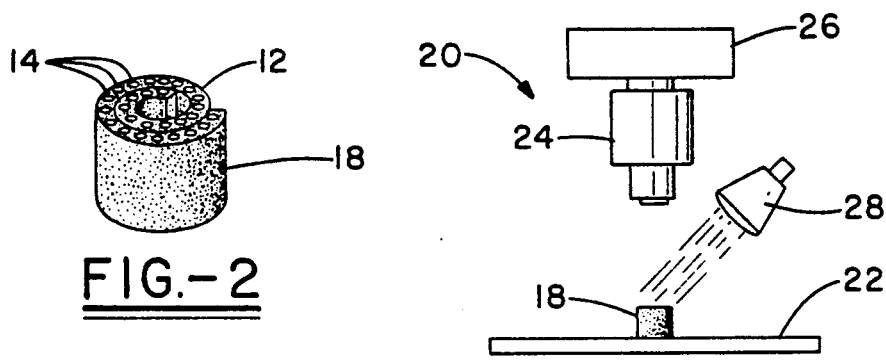
FIG.-2
FIG.-3
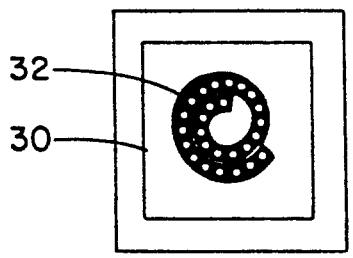
FIG.-4
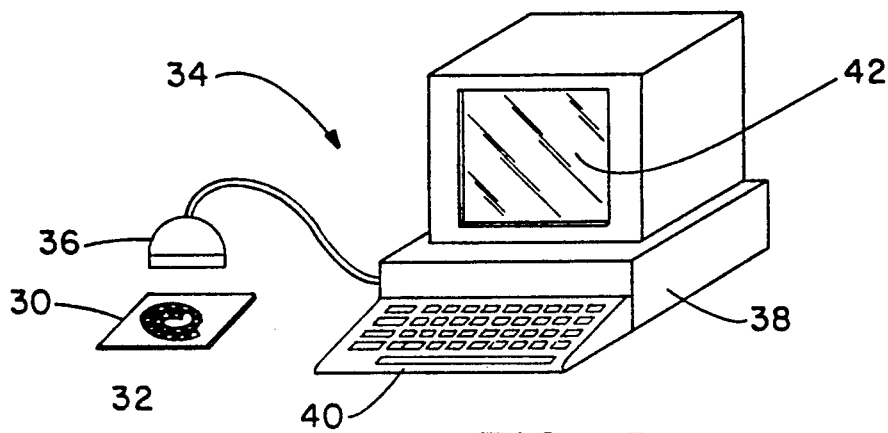
FIG.-5

METHOD AND APPARATUS FOR DETERMINING BODY PLY CORD DISTRIBUTION

TECHNICAL FIELD

The invention herein resides in the art of techniques and apparatus for determining the uniformity of the distribution of components in a fabrication. Particularly, the invention relates to such a technique and apparatus for determining the distribution of cords in a fabric composite. More specifically, the invention pertains to a technique and apparatus for determining the distribution of cords in a tire ply as the same is embodied in the manufacturing of a tire.

BACKGROUND ART

It is well known that in the construction of a pneumatic tire, a plurality of tire plies are layed up on a tire building drum. Such plies are formed from calendered fabric sheets in which cords of steel, polyester, or other appropriate materials are embedded in a rubber or elastomeric sheet. Those skilled in the art readily understand that such calendered fabric sheets provide the plies which are employed as the primary fortification or reinforcement of pneumatic tires during both manufacture and in use.

It has been found that tire integrity, uniformity, durability, and performance are a function of the uniformity of the distribution of the cords within the calendered fabric sheets from which the plies are formed. Accordingly, it is important to monitor such cord distribution in the calendered sheets to maintain the same within acceptable tolerances. In the prior art, such monitoring and measuring of the cord distribution has been totally manual. The previously known measurement methods have been slow, not always accurate, and time consuming. The prior processes and techniques have not been given to ease of locating the centers of the cords and, accordingly, measurements of cord distribution have been generally taken with respect to the outer surfaces of the cord, which measurement techniques have been found to be highly subjective in nature and, accordingly, not always accurate. There is a need in the art for an apparatus and technique for determining cord distribution in a fabric ply sheet which is accurate, reliable, and quickly and automatically achieved.

DISCLOSURE OF INVENTION

In light of the foregoing, it is a first aspect of the invention to provide a method and an apparatus for determining body ply cord distribution which are automated.

Another aspect of the invention is the provision of a method and an apparatus for determining body ply cord distribution which are highly accurate.

Still a further aspect of the invention is the provision of a method and an apparatus for determining body ply cord distribution which determine the center of each cord and, based upon the location of such centers, determine the spacing and distribution of the cords on a center-to-center basis.

Yet another aspect of the invention is the provision of a method and an apparatus for determining body ply cord distribution which employ a non-contacting measurement.

An additional aspect of the invention is the provision of a method and an apparatus for determining body ply cord distribution which are easy to implement with state of the art apparatus and techniques.

The foregoing and other aspects of the invention, which will become apparent as the detailed description proceeds, are achieved by an apparatus for determining body ply cord distribution in a calendered fabric sheet, comprising: first means for receiving a sample of said calendered sheet, said sample having an end exposing ends of the cords in spaced apart cross section; second means for casting light upon said cross sectional ends of said cords; third means for generating a digitized image of said sample end illuminated by said second means; and fourth means receiving said digitized image, determining a location of each of said ends of the cords within the sample end, and determining therefrom a spacing between adjacent cords within said sample.

Other aspects of the invention which will become apparent herein are attained by a method for determining body ply cord distribution in a calendered fabric sheet, comprising: preparing a sample piece of said calendered sheet having ends of cords extending normal to and exposed at an end of said sample piece; illuminating said end of said sample piece; preparing a digitized image of said end of said sample piece; and analyzing said digitized image and determining therefrom the distribution of said cords in said calendered sheet.

DESCRIPTION OF DRAWINGS

For a complete understanding of the objects, techniques, and structure of the invention reference should be made to the following detailed description and accompanying drawings wherein:

FIG. 1 is an illustrative view of a sheet of calendered fabric ply material showing test samples cut therefrom;

FIG. 2 is an illustrative view of a test sample of the ply material of FIG. 1;

FIG. 3 is an illustrative view of a microscopic photographic apparatus employed to generate a video image of an end of the test sample of FIG. 2;

FIG. 4 is a front elevational view of a photograph of an end of the sample roll of FIG. 2, taken with the apparatus of FIG. 3;

FIG. 5 is a scanner and microprocessor for scanning and digitizing the image of the photograph of FIG. 4 and processing the data therefrom;

BEST MODE FOR CARRYING OUT THE INVENTION

Figure 6:
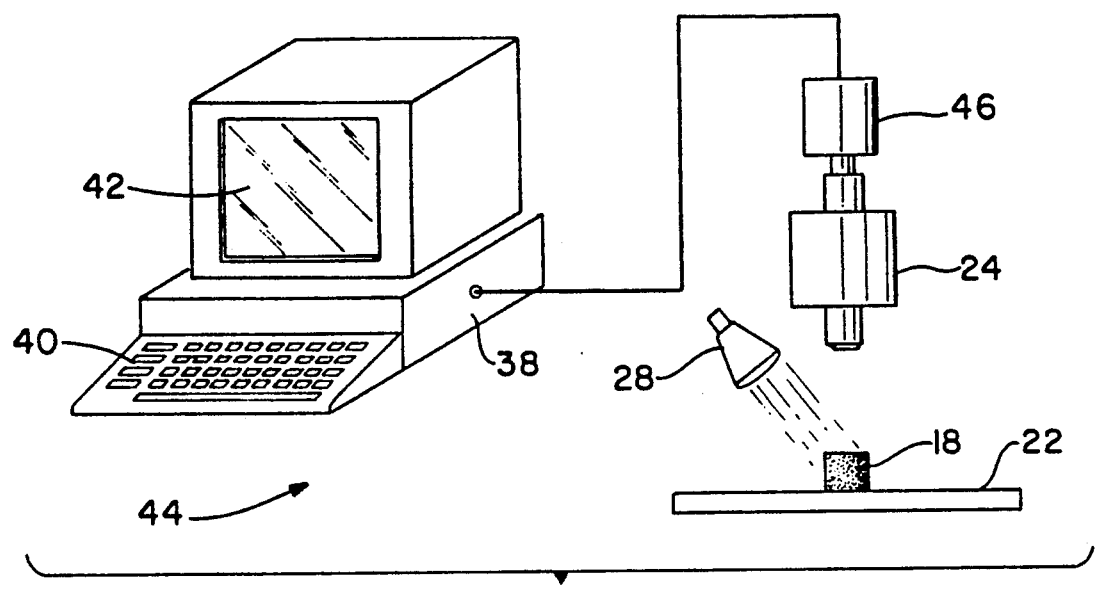
FIG. 6 is an alternate embodiment of the invention employing a vidicon or CCD for generating the digitized image of the test roll of FIG. 2.

Referring now to the drawings and more particularly FIG. 1, it can be seen that an elongated calendered fabric sheet of the type employed for forming the plies of a pneumatic tire is designated generally by the numeral 10. While the fabric sheet 10 is illustrated and described herein with respect to the manufacture of tires, it will be understood that the concept of the invention is applicable for monitoring the cord distribution in calendered fabric sheets employed in the manufacture of various types of reinforced elastomeric products, regardless of their end use. In any event, the calendered fabric sheet 10 comprises a rubber or other elastomeric material base 12 having a plurality of cords 14 extending longitudinally within the sheet 10 and parallel to each other.

As shown in FIG. 1, samples 16 are cut from the calendered sheet 10. While the samples 16 may be of various sizes and configurations, in the preferred embodiment a strip of sample material is cut transverse of the sheet 10, preferably 10 mm in length.

As shown in FIG. 2, the samples 16 are formed in the shape of a roll by wrapping them around a mandrel or other appropriate cylindrical structure. In a preferred embodiment of the invention, the mandrel employed for forming the roll 18 has a diameter of approximately 60 mm. It will be appreciated that the roll 18 is thus characterized by a sheet of rubber or elastomeric material 12 wrapped upon itself with cords 14 extending parallel to the axis of the roll 18 and parallel to each other.

The roll 18 is then submitted to an image generating system 20 which is employed for creating a video image of the spiral defined by an end of the roll 18. In the system 20, a base 22 receives the roll 18 thereon with the central axis of the roll 18 being normal to the base 22. Accordingly, the spiral of the opposite end is maintained beneath a microscope 24 which is interconnected with a photographic camera 26. It has been found that polyester cords of the type often used in tire manufacture are highly reflective to polarized light. Accordingly, a polarized light source 28 is positioned above the base 22 in such a manner as to cast polarized light upon the exposed spiral end of the roll 18, causing the cut ends of the cords 14 to be readily distinguished against the black background of the elastomeric base 12. In the preferred embodiment, an appropriate filter is employed with the camera 26 to enhance the contrast between the cut cross sectional surfaces of the cords 14 against the background of the elastomeric sheet material 12.

As shown in the FIG. 4, a photograph 30 is generated by the camera 26 of the spiral end of the roll 18. The image 32 of the spiral end demonstrates the presence of cords 14 in the rubber base 12, the cords 14 being of a bright white color, while the base 12 is black.

A digital processing system 34 of the type shown in FIG. 5 is next employed to analyze and process the information maintained in the image 32 of the photograph 30. The digital processing system 34 includes a scanner 36 interconnected with a microprocessor 38 having an associated keyboard 40 and video display 42. The scanner 36 serves to view the photograph 30 and to digitize the image 32. Those skilled in the art will appreciate that the process of digitizing simply comprises the steps of dividing the field of view into discrete picture elements known as pixels, and attributing to each a weighted value or gray level. Accordingly, the microprocessor 38 receives a matrix of digitized picture elements or pixels which corresponds to the image 32.

Since the process of the instant invention is most interested in determining the location and spacing of the cords 14 within the rubber sheet 12, it is simply necessary to distinguish between the highly reflective cross sectional ends of the cords 14 and the black nonreflective rubber background sheet 12. It has been found that a simple threshold may be employed by the microprocessor 38, such that pixels having a value above the threshold correspond to the cords 14, while those below the threshold correspond to the elastomeric sheet 12. Since the weighted values of the pixels of the cords and rubber background are significantly separated from each other, the establishment of an appropriate threshold is a simple matter.

Employing standard data processing techniques, the peripheral geometry or cross sectional area of each of the cords 14 can be readily identified and, knowing such geometry or area, the center point of the cord within the matrix can also be determined. Accordingly, knowing the location of the center point of each of the cords, the spacing between adjacent cords can be easily determined on a center-to-center basis. Further, by establishing a threshold of separation between cords, it can readily be determined whether the spacing of the cords 14 within the calendered fabric sheet 10 satisfies the established criteria. The results of such analysis can readily be displayed upon the screen 42 or can be printed out by means of a printer (not shown) or other devices. Additionally, the test data may be permanently stored on an associated disc.

With reference now to FIG. 6, it will be readily appreciated that the still camera 26 may readily be replaced by a digitizing camera 46, obviating the need for the scanner 36. In such embodiment, the digitizing camera 46 would typically comprise a vidicon or a charge coupled device (CCD). The output of the device 46 comprises the requisite matrix of digitized pixels, which matrix of gray level values is fed directly from the digitized image generating device 46 to the microprocessor 38. The processing of the data then proceeds as discussed above.

Figure 7A:
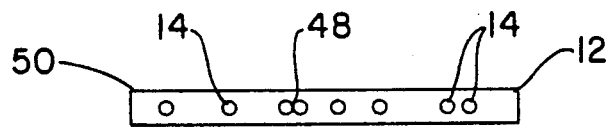
FIG. 7A is a top plan view of a portion of the test sample of FIG. 2.

As shown in FIG. 7A, a portion of a viewed section 50 of an end of the roll 18 is shown having cords 14 distributed therealong. Such would comprise a portion of the actual image viewed by the camera 26 or digital image generating device 46. As shown, the cords 14 are not necessarily uniformly spaced, and may even comprise a pair of cords 48 in actual abutting relationship.

Figure 7B:
FIG. 7B is a graph showing the gray level distribution of the view of FIG. 7A.

FIG. 7B illustrates a gray level distribution curve 52 as processed by the microprocessor 38, showing the gray level distribution along the viewed section 50. Each of the cords 14 demonstrates a high gray level value, corresponding to white, while the lower section or base corresponds to the black elastomeric material 12. A transition between black and white defines the transition of the spikes of the distribution curve of FIG. 7B.

Figure 7C:
FIG. 7C is a digitized distribution of the gray level of FIG. 7B.

As shown in FIG. 7C, the gray level value of the distribution curve 52 of FIG. 7B may be compared against a threshold to distinguish between the white highly reflective surfaces of the cross sectional ends of the cords 14 and the remaining black portion of the elastomeric base material 12. Finally, in FIG. 7D the distribution graph 56 locates the midpoint of each of the cords 18 as defined by the center point of the digitized data of FIG. 7C. It will be observed from FIGS. 7A-7D that the pair of cords 48, representing a large white area in the digitized distribution curve 54, defines two center points as shown in FIG. 7D.

Figure 7D:
FIG. 7D is a distribution graph of the center points of the cords of the ply sample of FIG. 2 as determined from the digitized distribution of FIG. 7C.

Using the distribution of FIG. 7D, the spacing between each of the center points along the distribution curve 56 can be readily ascertained. If the distribution between adjacent center points falls above or below predetermined thresholds, and the same is noted upon the video display 42, a determination can be made of the uniform distribution of a reinforcing member for appropriate subsequent action.

Thus it can be seen that the objects of the invention have been satisfied by the structure presented above. While in accordance with the patent statutes only the best mode and preferred embodiment of the invention has been presented and described in detail, it is to be understood that the invention is not limited thereto or thereby. Accordingly, for an appreciation of the true scope and breadth of the invention reference should be made to the following claims.

What is claimed is:

1. Apparatus for determining body ply cord distribution in a calendered fabric sheet, comprising:
   first means for receiving a sample of said calendered sheet, said sample having an end exposing ends of the cords in spaced apart cross section;
   second means for casting light upon said cross sectional ends of said cords;
   third means for generating a digitized image of said sample end illuminated by said second means; and
   fourth means for receiving said digitized image, determining a location of each of said ends of the cords within the sample end and determining therefrom a spacing between adjacent cords within said sample.

2. The apparatus according to claim 1, wherein said second means comprises a polarized light source.

3. The apparatus according to claim 2, wherein said third means comprises a camera viewing said end of said sample through a microscope.

4. The apparatus according to claim 3, wherein said camera generates a photographic image of said end of said sample illuminated by said polarized light source.

5. The apparatus according to claim 4, wherein said third means further comprises a video scanner for digitizing said photographic image.

6. The apparatus according to claim 5, wherein said fourth means comprises a digital processing means for determining locations of images of said ends of said cords in said digitized photographic image and determining a distribution spacing between said cords therefrom.

7. The apparatus according to claim 6, wherein said digital processing means determines a center point for each of said ends of said cords and establishes said distribution of spacings between said cords as a function of locations of said center points.

8. The apparatus according to claim 2, wherein said third means comprises a digitized video imaging device generating said digitized image as an array of pixels.

9. The apparatus according to claim 8, wherein said fourth means comprises a digital processing means receiving said digitized image and determining locations of the center points of each of said cords therefrom.

10. The apparatus according to claim 8, wherein said fourth means determines a distribution of said cords as a function of said locations of each of said center points.

11. A method for determining body ply cord distribution in a calendered fabric sheet, comprising:
    preparing a sample piece of said calendered sheet having ends of cords extending normal to and exposed at an end of said sample piece;
    illuminating said end of said sample piece;
    preparing a digitized image of said end of said sample piece; and
    analyzing said digitized image and determining therefrom the distribution of said cords in said calendered sheet.

12. The method according to claim 11, wherein said step of illuminating comprises casting polarized light onto said end of said sample piece.

13. The method according to claim 12, wherein said step of determining the distribution of said cords comprises determining a center point of each said end of each said cord.

14. The method according to claim 13, wherein said step of determining the distribution of said cords further comprises determining a separation between said center points of adjacent cords.

15. The method according to claim 14, wherein said step of preparing a sample piece comprises cutting a piece from said calendered sheet and forming a spiral roll from said piece, said ends of said cords being exposed at an end of said roll.

16. The method according to claim 14, wherein said digitized image is prepared by photographing said end of said sample piece.

17. The method according to claim 16, wherein said photograph of said sample piece is scanned and digitized into a matrix of pixels.

18. The method according to claim 14, wherein said digitized image is prepared by a digitized video imaging device.

19. The method according to claim 18, wherein said digitized image comprises a matrix of pixels having associated gray level values.

20. The method according to claim 19, wherein said pixels are compared with a threshold, pixels exceeding said threshold being determined as comprising a cord.

* * * * *